United States Patent [19]

Osaki

[11] Patent Number: 5,001,433
[45] Date of Patent: Mar. 19, 1991

[54] APPARATUS AND METHOD FOR MEASURING ELECTRIC CHARACTERISTICS OF MATERIAL

[75] Inventor: Shigeyoshi Osaki, Takarazuka, Japan
[73] Assignee: Kanzaki Paper Manufacturing Co., Ltd., Tokyo, Japan
[21] Appl. No.: 339,793
[22] Filed: Apr. 18, 1989

[30] Foreign Application Priority Data

Apr. 22, 1988 [JP] Japan .................. 63-100999

[51] Int. Cl.⁵ .................. G01R 27/04; G01N 22/00
[52] U.S. Cl. .................. 324/632; 324/639; 324/642; 73/159
[58] Field of Search .................. 73/159; 324/632, 639, 324/641, 642

[56] References Cited

U.S. PATENT DOCUMENTS

| | | | |
|---|---|---|---|
| 3,025,463 | 3/1962 | Luoma | 324/642 |
| 3,562,642 | 2/1971 | Hochschild | 324/639 |
| 4,097,796 | 6/1978 | Lunden | 324/642 |
| 4,350,883 | 9/1982 | Lagarde | 374/642 |
| 4,581,575 | 4/1986 | Osaki | 73/159 |
| 4,612,807 | 9/1986 | Wunderer | 73/159 |
| 4,674,325 | 6/1987 | Kiyobe | 73/159 |
| 4,710,700 | 12/1987 | Osaki | 73/159 |
| 4,781,063 | 11/1988 | Osaki et al. | |
| 4,789,820 | 12/1988 | Parrent | 73/159 |
| 4,841,223 | 6/1989 | Baum | 73/159 |

FOREIGN PATENT DOCUMENTS

| | | | |
|---|---|---|---|
| 61-83946 | 4/1986 | Japan . | |
| 1190242 | 11/1985 | U.S.S.R. | 324/58.5 A |
| 1355942 | 11/1987 | U.S.S.R. | 324/58.5 A |

Primary Examiner—Reinhard J. Eisenzopf
Assistant Examiner—Jose M. Solis
Attorney, Agent, or Firm—Morgan & Finnegan

[57] ABSTRACT

Apparatus and method for measuring electric characteristics of sheet-like materials using an instrument which includes a waveguide tube member having one end connected to transmitter for introducing a microwave into the tube member and the other end fully opened, a waveguide terminal member having an opened end facing the opened end of the tube member to form slit of the whole wave guide body constituted from the tube and terminal members and having the other end connected to first microwave detector, and an auxiliary waveguide branching from the wall portion of said tube member adjacent to the slit with the branch-extension end being associated with a second microwave detector.

2 Claims, 1 Drawing Sheet

APPARATUS AND METHOD FOR MEASURING ELECTRIC CHARACTERISTICS OF MATERIAL

TECHNICAL FIELD

The present invention relates to an apparatus and method for measuring electric characteristics of material by applying electromagnetic microwaves.

BACKGROUND ART

Conventionally, there is such a system as proposed for detecting variations of resonant frequency and Q value of a cavity resonator when a sheet-like material is inserted therein, in order to measure complex dielectric constant of the material by applying microwaves. However, this system is not suited for measuring the electric conductivity of sheet-like conductive material containing carbon fiber. When the conductive material is inserted in a cavity resonator systems, the resonant condition is destroyed, and thus, even if a driving power input were sufficiently large, for the system it is extremely difficult to quantitatively detect the difference of conductivity between materials. On the other hand, carbon fiber is distinctly useful for reinforcing plastic material. Actually, carbon-fiber-reinforced plastic material is widely used today. Reflecting this, those who are concerned in this field look for a simplified method for comparatively measuring the ratio of content and degree of orientation of carbon fiber in the plastic material. Measurement of these can be achieved by applying mechanical means which first cuts off specimen having the predetermined size from the product material in various directions before carrying out tension tests. Nevertheless, measurement of those factors mentioned above requires many processes and much time and labor. Furthermore, when comparatively evaluating the conductivity between materials to satisfy the needs for applying the conductivity of material like in the case, for example of shielding the electromagnetic field, the test method mentioned above is totally useless, since the conductivity of material can not be detected by such method.

DISCLOSURE OF THE INVENTION

Accordingly a principal object of the invention is to provide a novel apparatus which is capable of easily and simply measuring the conductivity of conductive material by means of microwaves.

Another object of the invention is to provide novel and effective method for the above measurement by means of microwaves. To achieve the above objects, the first aspect of the invention provides an apparatus for measuring electric characteristics of sheet-like materials comprising: a main waveguide for guiding a microwave therein; means connected to one of the opposite ends of said main waveguide, for introducing the microwave thereto: a slit formed across the intermediate portion of said waveguide between the opposite ends thereof for accomodating a sheet-like material to be inspected; first detector means connected to the other end of said main waveguide for detecting a transmitted microwave through the sheet-like material accomodated into said slit; an auxiliary waveguide connected at one end thereof to a directional coupler located on the wall portion of said main waveguide adjacent to said slit at the microwave introducing side for admitting the microwave from said main waveguide: and second detector means connected to the other end of said auxiliary waveguide for detecting a reflected microwave from the sheet-like material accomodated into said slit: and whereby electric characteristics of the sheet-like material is determined from the relations between an input microwave intencity and its sheet-transmitted intencity and/or between the input microwave intencity and its sheet-reflected intencity.

The second aspect of the invention provides a method for measuring electric characteristics of sheet-like materials using an instrument which includes a waveguide tube member having one end connected to means for introducing a microwave into said tube member and the other end fully opened, and an auxiliary waveguide branching from the wall portion of said tube member adjacent to said opened end with the branch-extension end being associated with microwave detector means, said method comprising the steps of:

placing a sheet-like material to be inspected to substantially abut on said opened end of said tube member:

energyzing said microwave introducing means to generate a microwave in said tube member and to direct it onto the sheet-like material substantially abutting on said opened end;

detecting a reflected microwave entered said auxiliary waveguide from said sheet-like material by said detector means: and determining electric characteristics of the sheet-like material in accordance with the relation between an input microwave intencity by said introducing means and the intencity of the reflected microwave from the material.

The third aspect of the invention provides a method for measuring electric characteristics of sheet-like materials which is represented by higher electric conductivity than that by the second aspect, the method using the above instrument also including a waveguide terminal member having an opened end facing said opened end of said tube member to form slit of the whole waveguide body constituted from said tube and terminal members and having the other end connected to first microwave detector means, and determining electric characteristics of the sheet-like material in accordance with the relation between an input microwave intencity by said introducing means and the intencity of the reflected microwave entered into the auxiliary waveguide from the material, and between the input microwave intencity and the intencity of the transmitted microwave entered into the waveguide terminal member through the material.

DETAILED DESCRIPTION OF THE INVENTION

Figure 1:
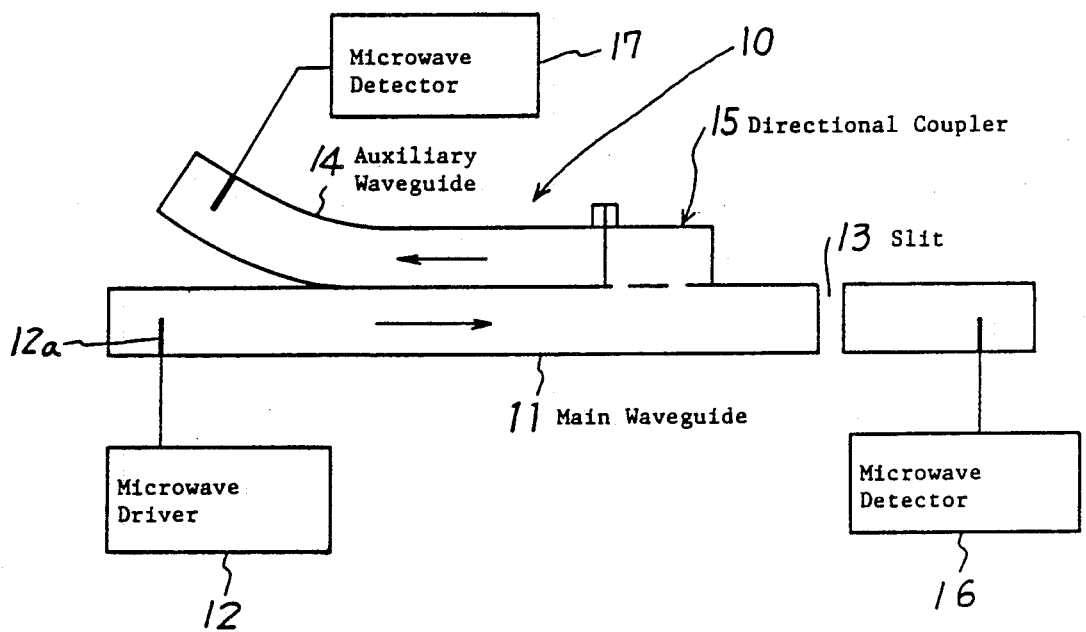
FIG. 1 is a lateral view showing general structure of the embodied apparatus for measuring electric characteristic of material according to the invention with the block diagram of the associated circuit.

As shown in FIG. 1, an apparatus 10 embodied by the invention is provided with an antenna or probe 12a of a driving circuit as microwave-introduction means 12 at the left-end as shown of the waveguide 11 and also with a slit 13 which traverses the waveguide 11 in the halfway at a distance of the substantial length of the waveguide 11 from the left-end for allowing insertion of the specimen through it. An auxiliary waveguide 14 is secured on the left or major portion of slit 13 shown in FIG.1, i.e., the auxiliary waveguide 14 is connected through a directional coupler 15 to the side at which microwave is irradiated to the specimen. Wave detectors 16 and 17 are respectively provided at the ends of the waveguides 11 and 14. To detect transmitting microwaves through the specimen using the wave-detector 16, any non-reflection material is set to the left end of the auxiliary waveguide 14. On the other hand, to detect reflected microwave using the wave-detector 17, it is preferred that any non-reflection material be set to the right end of the waveguide 11 in order that the reflected microwave from the waveguide 11 other than the one 14 corresponding to the wave-detector 17 can be prevented from being detected.

When no specimen is present in the slit 13, a microwave propagates itself to the right inside of the waveguide 11. When inserting the specimen into the slit 13, if the specimen is dielectric without bearing conductivity and has the thickness which is quite thinner than the wave length of microwave inside of the waveguide 11, condition of the microwave propagating inside of the waveguide 11 remains constant, and thus, wave detectors 16 and 17 respectively generate constant output signals. Concretely, the transmission factor of microwave through the specimen is close to about 100%, whereas the reflection factor is close to about 0%. On the other hand, when inserting the conductive sheet containing carbon fiber into the slit 13, a part of microwave is reflected by the conductive specimen, another part of which is transmitted through the specimen, and the other part is absorbed by it, thus the signal level output from the wave-detector 16 being low, while a comparatively high output signal appears at the wave-detector 17. This facilitates a user to measure the transmission factor and the reflection factor of the specimen. Both of these factors are variable by the conductivity of the specimen, and thus, the user can also measure the conductivity by preliminarily making calibration. If the user need to merely execute comparative measurement of the conductivity, he can comparatively evaluate the conductivity of specimens by preparing the reference specimen.

Figure 2:
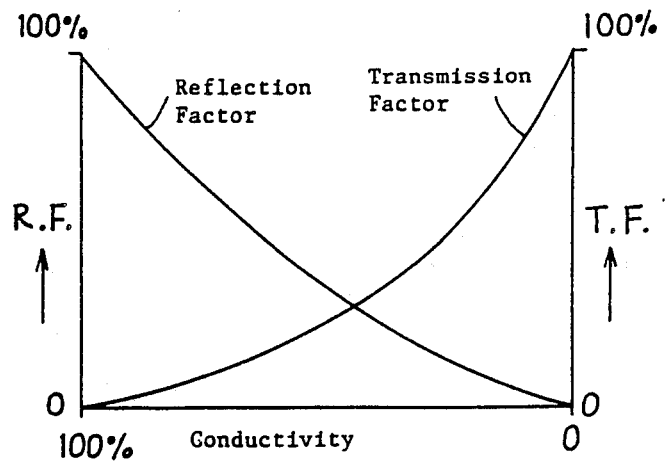
FIG. 2 is a graphical chart representing the relationship between the conductivity and the reflection factor/transmission factor of the sample.

As shown in FIG. 2, if the specimen shows extremely large conductivity and metallic characteristic, then its reflection factor rises, whereas the transmission factor and the absorption characteristic diminish to a very low level. Conversely, if the specimen is formed of a good insulating material and shows extremely low conductivity, the reflection factor and the absorption characteristic diminish, and conversely, the transmission factor extremely rises. Thus, if the absorption curve (absorption/conductivity factor) is given, then either the transmission factor or the reflection factor is measured so that the user can derive the non-measured factor from the either of these factors. In this case, only the wave-detector 16 is provided on the wave-permeation or transmitted side without providing auxiliary waveguide 14 (see FIG. 1), or only the wave-detector 17 is provided at the end of the auxiliary waveguide 14 without providing wave detection means on the wave-permeation side. Since the wave reflection at the end of the waveguide does not adversely affect the measurement effect, the user can execute measuring operations by applying the system which eliminates all the components shown to the right of slit 13 (see FIG. 1). In this case, the right end of the substantial tube body of the waveguide 11 is open, and thus, reflected microwave is present on the open surface even when no specimen is set. When the open surface of the right-end of the substantial tube body of the waveguide 11 is covered with a conductive specimen, if the conductivity is very high, the reflection factor extremely rises. When the conductivity is low, the refleciton factor approximates the value which is present when the right end of the waveguide tube body is open. This allows the user to properly measure the conductivity of the specimen.

DESCRIPTION OF THE PREFERRED EMBODIMENTS

When providing the slit 13 within the waveguide 11 as shown in FIG. 1, into which the specimen is inserted, the inventors first checked if the position of the slit 13 could adversely affect the propagation of microwave inside of the wave guide 11, or not. The inventors fixed the length of the left part of the waveguide 11 shown in FIG. 1 to be 1 meter from the position of slit 13 having 1.9 mm of width. The inventors then varied the length of the right part of the waveguide 11 in a range from 1 cm to a maximum of 20 cm. As a result, the inventors confirmed that the level of signals output from the wave detector remained almost constant. Conversely, inventors then fixed the length of the right part of the waveguide 11 to be 10 cm from the position of the slit 13, and then varied the length of the left part in a range from 10 cm to a maximum of 150 cm. Like the above case, inventors confirmed that the level of signals output from the waveguide 11 did not vary at all. The inventors then varied the width of the slit 13 in a range from zero to a maximum of 7 mm. When the slit 13 was provided with 7 mm of the width against 0 mm of the reference, the level of signals output from the wave-detector 16 is lowered by 6.5 dB. It proves that the narrower the width of the slit 13, the better the stability of the signal level output from the wave-detector 16. This is probably because microwave leaks through the slit 13 simultaneous with the reflection of microwave caused by presence of slit 13.

EXAMPLE 1

Based on the constitution as shown in FIG. 1, the inventors assembled the apparatus composed of the main waveguide with a size of 29.1 mm × 58.1 mm and a slit with a width of 4 mm. The inventors inserted a specimen sheet made from poly(ethylene terephthalate) fiber with a thickness of 100 microns into the prepared slit. Finally, the inventors confirmed by comparison with the output signal level prior to the insertion of the specimen that the level of signals output from the wave-detector 16 remained constant.

EXAMPLE 2

The test for the second example was executed by means of the same apparatus as that was used for the first example. The inventors prepared a specimen sheet made from non-woven carbon-fiber cloth with a weight of 34.6 g./m$^2$, and then inserted the specimen into the slit. The inventors then checked the level of signals output from the wave-detectors 16 and 17 at some directions by rotating the specimen in its plane. The test result is described below. The inventors set angles of the rotation of the specimen based on the direction of the short-part of the waveguide 11, i.e., in the direction of the electric field.

| Angles of rotation of the specimen | Permeation or transmitted output (n W) | Reflective output (μW) |
| --- | --- | --- |
| 0° | 6.38 | 0.604 |
| 45° | 17.8 | 0.544 |
| 90° | 32.3 | 0.430 |

The inventors confirmed that non-woven carbon-fiber cloth has distinct fiber-orientation characteristic.

EXAMPLE 3

The test for the third example was executed by means of the same apparatus as that was used for the above examples with an exception in which the right part of the waveguide 11 was disengaged from the slit 13 to provide an open-end surface for the substantial tube body of the waveguide 11. The inventors checked the conductivity of the organic conductive sheet made from a non-woven carbon-fiber cloth inserted in plastic films, where the specimen in a plastic film fully covered the open-end of the waveguide 11. The inventors set a dielectric sheet by pressing it against the back of the specimen for stabilizing it. Since a part of microwave transmitted through the specimen, it is essential for the system to stabilize means for tightly pressing the specimen against the open-end of the waveguide tube body because the stability of the specimen critically affects the measurement of the reflected microwave. The test result of the third example is shown below. Like the above case, the inventors confirmed that non-woven carbon-fiber cloth had distinct fiber-orientation characteristic.

| Angles of rotation of the specimen | Reflective output (μW) |
| --- | --- |
| 0° | 0.812 |
| 45° | 0.680 |
| 90° | 0.626 |

Using the open-end waveguide tube like in the third example, the user can easily set the specimen to the apparatus having the structure mentioned above, and thus, the user can execute measurement against a web without cutting off a specimen from it. The apparatus embodied by the invention allows the user to execute measurement not only against sheet-like material, but he can also do it against a thick object as well. Furthermore, the apparatus allows the user to execute measuring operations by bringing the open-end of the waveguide into contact with the surface of a structured object or across the predetermined minimal clearance.

INDUSTRIAL APPLICABILITY

According to the invention, the apparatus allows a user to easily measure the conductivity and the anisotropy of conductive materials like conductive plastic objects. In particular, the user can easily insert the specimen into the apparatus by bringing the specimen into contact with the open end of the waveguide tube, and yet, the user can easily rotate the specimen as required. Furthermore, the apparatus embodied by the invention offers useful advantage in allowing the user to measure electric characteristic of those specimens formed of an web and/or a solid body composition and those specimens having substantially wide area without the need for cutting off the specimen from them.

What is claimed is:

1. An apparatus for measuring electric characteristics of sheet-like materials comprising:
   a main waveguide for guiding a microwave therein:
   means connected to one of the opposite ends of said main waveguide, for introducing the microwave thereto;
   a slit formed across the intermediate portion of said waveguide along a cross section thereof for accomodating a sheet-like material to be inspected;
   first detector means connected to the other end of said main waveguide for detecting a transmitted microwave through the sheet-like material accomodated into said slit:
   an auxiliary waveguide connected at one end thereof to a directional coupler located on the wall portion of said main waveguide adjacent to said slit at the microwave introducing side for admitting the microwave from said main waveguide; and
   second detector means connected to the other end of said auxiliary waveguide for detecting a reflected microwave from the sheet-like material accomodated into said slit: and
   whereby electric characteristics of the sheet-like material is determined from the relations between an input microwave intensity and its sheet-transmitted intensity and/or between the input microwave intensity and its sheet-reflected intensity.

2. A method for measuring electric characteristics of sheet-like materials using an instrument which includes a waveguide tube member having one end connected to means for introducing a microwave into said tube member and the other end fully opened with the edge of the opened end perpendicular to the longitudinal direction of the tube, a waveguide terminal member having an opened end facing said opened end of said tube member to form slit of the whole waveguide body constituted from said tube and terminal members and having the other end connected to first microwave detector means and an auxiliary waveguide branching from the wall portion of said tube member adjacent to said slit with the branch-extension end being associated with second microwave detector means, said method comprising the steps of:
   inserting a sheet-like material to be inspected into said end of said tube and terminal members;
   energyzing said microwave introducing means to generate a microwave in said tube member and to direct it onto the sheet-like material between said opened ends:
   detecting a transmitted microwave entered said terminal member through the sheet-like material by said first detector means;
   detecting a reflected microwave entered said auxiliary waveguide from the sheet-like material by said second detector means: and
   determining electric characteristics of the sheet-like material in accordance with the relations between an input microwave intensity by said introducing means and the intencity of the reflected microwave from the material, and between the input microwave intensity and the intensity of the transmitted microwave through the material.

* * * * *